(12) United States Patent
Zhang et al.

(10) Patent No.: US 10,357,685 B2
(45) Date of Patent: Jul. 23, 2019

(54) TRAINING GARMENT FOR PERSON SUFFERING FROM UPPER LIMB DYSFUNCTION

(71) Applicant: KONINKLIJKE PHILIPS N.V., Eindhoven (NL)

(72) Inventors: Jianxiong Zhang, Shanghai (CN); Yugang Jia, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1171 days.

(21) Appl. No.: 14/400,632

(22) PCT Filed: May 14, 2013

(86) PCT No.: PCT/IB2013/053900
§ 371 (c)(1),
(2) Date: Nov. 12, 2014

(87) PCT Pub. No.: WO2013/171662
PCT Pub. Date: Nov. 21, 2013

(65) Prior Publication Data
US 2015/0125837 A1    May 7, 2015

(30) Foreign Application Priority Data

May 16, 2012    (WO) ................ PCT/CN2012/075572

(51) Int. Cl.
*A63B 24/00*    (2006.01)
*A61B 5/11*    (2006.01)
(Continued)

(52) U.S. Cl.
CPC ........ *A63B 24/0003* (2013.01); *A61B 5/1127* (2013.01); *A61B 5/6824* (2013.01);
(Continued)

(58) Field of Classification Search
CPC . G09B 19/003; A61F 5/0118; A41D 2400/32; A63B 2209/19; A63B 69/3608; A63B 24/0003
See application file for complete search history.

(56) References Cited

U.S. PATENT DOCUMENTS 5,319,806 A    6/1994 Hermann et al.
5,409,500 A *  4/1995 Dyrek ...................... A61F 7/10
                                                        607/111
(Continued)

FOREIGN PATENT DOCUMENTS

CA    2467545 A1    5/2004
FR    2784301 A1    4/2000
(Continued)

OTHER PUBLICATIONS

Tognetti, A., et al.; Wearable kinesthetic system for capturing and classifying upper limb gesture in post-stroke rehabilitation; 2005; Journal of NeuroEngineering and Rehabilitation; 2(8)1-16.

*Primary Examiner* — Jerry-Daryl Fletcher

(57) ABSTRACT

The present invention provides a training garment (1) for persons suffering from upper limb dysfunction. According to one aspect of the invention, the training garment (1) comprises a shoulder garment (10), which comprises a shoulder portion (11) adapted to be worn across a person's shoulder and a first main body portion (12) adapted to be worn around the trunk of the person. Both ends of the shoulder portion (11) are attached to the first main body portion (12), and the shoulder portion (11) has an area (101) for receiving a shoulder marker. The proposed training garment (1), due to its special design of the shoulder portion (11) and the first main body portion (12), can prevent displacement of the shoulder marker while the person is performing active rehabilitation exercises, such as raising up his arm, and (Continued)

therefore, it can improve the recognition accuracy of the movement tracking system for the rehabilitation training.

9 Claims, 4 Drawing Sheets

(51) Int. Cl.
    *A61F 5/37*      (2006.01)
    *A61B 5/00*      (2006.01)
    *G06K 9/00*      (2006.01)
    *G06K 9/32*      (2006.01)

(52) U.S. Cl.
    CPC .......... *A61B 5/6831* (2013.01); *A61F 5/3723* (2013.01); *G06K 9/00355* (2013.01); *G06K 9/3216* (2013.01); *A41D 2400/32* (2013.01); *A41D 2600/00* (2013.01); *A41D 2600/10* (2013.01); *A61B 2505/09* (2013.01); *G06K 2009/3225* (2013.01)

(56) References Cited

U.S. PATENT DOCUMENTS

| | | | | |
|---|---|---|---|---|
| 5,685,811 | A * | 11/1997 | McShane | A61F 5/0123 482/114 |
| 8,852,015 | B1 * | 10/2014 | Hoang | A63B 69/3608 473/212 |
| 2002/0111777 | A1 | 8/2002 | David | |
| 2003/0088385 | A1 | 5/2003 | David | |
| 2004/0025361 | A1 * | 2/2004 | Gile | A61B 5/1072 33/515 |
| 2007/0239091 | A1 | 10/2007 | Brockington et al. | |
| 2008/0161731 | A1 | 7/2008 | Woods et al. | |
| 2009/0300889 | A1 * | 12/2009 | Shiue | A44B 11/006 24/197 |
| 2011/0201476 | A1 * | 8/2011 | Solomon | G06F 19/00 482/8 |
| 2013/0050826 | A1 * | 2/2013 | Guyan | G06F 3/0325 359/518 |
| 2013/0292433 | A1 * | 11/2013 | Maguire | A45F 3/04 224/257 |

FOREIGN PATENT DOCUMENTS

| | | |
|---|---|---|
| WO | 2004/041379 | 5/2004 |
| WO | 2006113654 A1 | 10/2006 |
| WO | 2008/010131 | 1/2008 |
| WO | 2008/099301 | 8/2008 |
| WO | 2010097735 A1 | 9/2010 |

* cited by examiner

TRAINING GARMENT FOR PERSON SUFFERING FROM UPPER LIMB DYSFUNCTION

CROSS REFERENCE TO RELATED APPLICATIONS

This application is a national filing of PCT application Serial No. PCT/IB2013/053900, filed May 14, 2013, published as WO 2013/171662 A1 on Nov. 21, 2013, which claims the benefit of PCT application serial number PCT/CN2012/075572 filed May 16, 2012, which is incorporated herein by reference.

FIELD OF THE INVENTION

The present invention relates to a garment for rehabilitation training, especially to a training garment for a person suffering from upper limb dysfunction.

BACKGROUND OF THE INVENTION

Hand dysfunction is a common symptom, which may be caused by many conditions such as stroke or traumas resulting in brain injury. A lot of patients suffer from this, and it could seriously affect their life. Stroke alone causes 0.8 million people to become disabled every year in the U.S. There are around 1.5 million stroke survivors annually in China and 80% of them suffer from upper-limb (motor, sensation) dysfunction.

To help the patients to recover, different rehabilitation methods can be employed. One of these methods is known as Active Rehabilitation Exercise, the efficacy of which has been proven in many studies and which has been widely used by doctors and therapists. As a cost-effective solution, a movement tracking system based on an infra-red camera and retro-reflective markers can provide guidance and interaction in natural and intuitive ways. While the patient is doing active rehabilitation exercises, he/she can get guidance and encouragement from a system capable of tracking the motion of the limb and giving real-time feedback.

For such a system, first, patients should wear a garment (usually covered by reflective material) covering their hands or upper limbs, which can be tracked by a special camera (e.g. infrared camera) in the recognition system. Second, they can do exercises under the guidance of demonstration examples shown on the computer screen or other display equipment. Meanwhile their training actions will be tracked by the special camera when they are doing exercises in front of the display screen. At the same time, the system can compare the tracked actions completed by patients with standard ones and give them feedback in order to correct their actions. Finally, the quality of the exercises performed can be estimated in a clinical way. So, in this manner, a long-term exercise and practice plan can help patients recover from hand and upper limb dysfunction.

FIG. 1 shows a training garment for persons with upper limb dysfunction. As shown in FIG. 1, the garment is designed as one piece, making it easy for a patient to put it on. However, in practice, it is mainly suitable for patients in a later-stage of the rehabilitation training, rather than for patients in an early-stage.

SUMMARY OF THE INVENTION

As mentioned above, the training garment as shown in FIG. 1 is not very suitable for patients in an early-stage of the rehabilitation training, since the inventors of the present invention recognize that for patients in different stages, the priority of garment design requirements is different.

For example, later-stage patients are capable of more advanced functional activities and usually can perform training by themselves. So, the garment for later-stage patients should be designed such that said patients can put it on by themselves. But as to early-stage patients, they always need a caregiver or relative who can help them to put it on.

Meanwhile, different tracking accuracy is required for patients in different stages. For later-stage patients, a certain level of tracking error is allowed based on feedback from clinicians. However, for early-stage patients, high-precision abnormal pattern detection is required.

Therefore, the training garment as shown in FIG. 1 cannot meet the high recognition accuracy criteria, which may be the first priority to be considered for the early-stage patients.

Specifically, if the training garment shown in FIG. 1 is used for the early-stage patients, the shoulder marker 100 will move when patients perform certain exercises (for example, shoulder abduction). This will lead to a false abnormal-pattern alarm (trunk movement). Furthermore, due to the one piece design, the dependent elbow marker 200 easily gives rise to inaccurate calibration because the movement tracking system always reads the distance between the elbow and the shoulder markers as that between shoulder and elbow joint, however the elbow marker 200 is not often in the position of the elbow joint.

Therefore, to ensure stability and accuracy of rehabilitation training, the training garment should be specifically designed for patients. As mentioned above, in order to meet specific technology requirements and this kind of patient requirements, shoulder and elbow markers must be fixed in the correct position. Especially, the shoulder marker must not be subject to obvious displacement with respect to the body of the patient in the training process. In addition, some other issues, such as, usability of the garment, fixation accessory design for the garment, and wearing process, should be considered at the same time.

In view of the above problems, one object of the present invention is to provide a training garment which can ensure that the shoulder marker is fixed in the correct position and which thus ensures rehabilitation-training stability and accuracy.

In accordance with an aspect of the present invention, there is proposed a training garment for persons suffering from upper limb dysfunction, comprising: a shoulder garment, which comprises: a shoulder portion, adapted to be worn across a person's shoulder; and a first main body portion, adapted to be worn around the trunk of the person, wherein both ends of the shoulder portion are attached to the first main body portion, and the shoulder portion has an area for receiving a shoulder marker.

Due to the special design of the shoulder portion and the first main body portion, the proposed training garment can prevent displacement of the shoulder marker while the person is doing active rehabilitation exercises, such as raising up his arm, and therefore, it can improve the recognition accuracy of the movement tracking system for the rehabilitation training.

In accordance with another aspect of the present invention, the training garment further comprises: an elbow garment which is separate from the shoulder garment and which comprises: a second main body portion, adapted to be worn around the upper limb of the person; and an elbow marker, which is attached to the second main body portion of the elbow garment and which is adapted to be worn around the upper limb of the person near the elbow joint.

In this design, since the elbow garment is separate from the shoulder garment, the independent elbow garment ensures correct and specific calibration, because the elbow marker can be accurately fixed at or near where the elbow joint is positioned, so that the movement tracking system can figure out the specific distance between the shoulder marker and the elbow marker. Its independent positioning instead of being attached to the shoulder garment removes the need for the patient or caregiver to correct its position.

Therefore, in this aspect, not only the shoulder marker's displacement can be prevented, but also the elbow marker can be accurately fixed. Accordingly, the recognition accuracy of the movement tracking system may be further improved.

In accordance with a further aspect of the present invention, the second main body portion further comprises a locating hole for receiving the elbow joint of the person.

In this design, the locating hole of the elbow garment may ensure both wearing accuracy and recognition accuracy. The locating hole functions as a mark designed specially to show the patient how to wear the elbow garment, i.e. placing the elbow joint in the locating hole is the only right way to wear the elbow garment. In this way, it helps the patient to fixate the elbow marker in the right position. Furthermore, in this way, more of the elbow marker's external superficial area becomes exposed instead of being hidden from view by the elbow joint. Accordingly, it can further improve the accuracy of recognition.

Various aspects and features of the disclosure are described in further detail hereinbelow. And other objects and advantages of the present invention will become more apparent and will be easily understood from the description with reference to the accompanying drawings.

DESCRIPTION OF THE DRAWINGS

The present invention will be described and explained hereinafter in more detail by means of embodiments and with reference to the drawings, in which.

Figure 1:
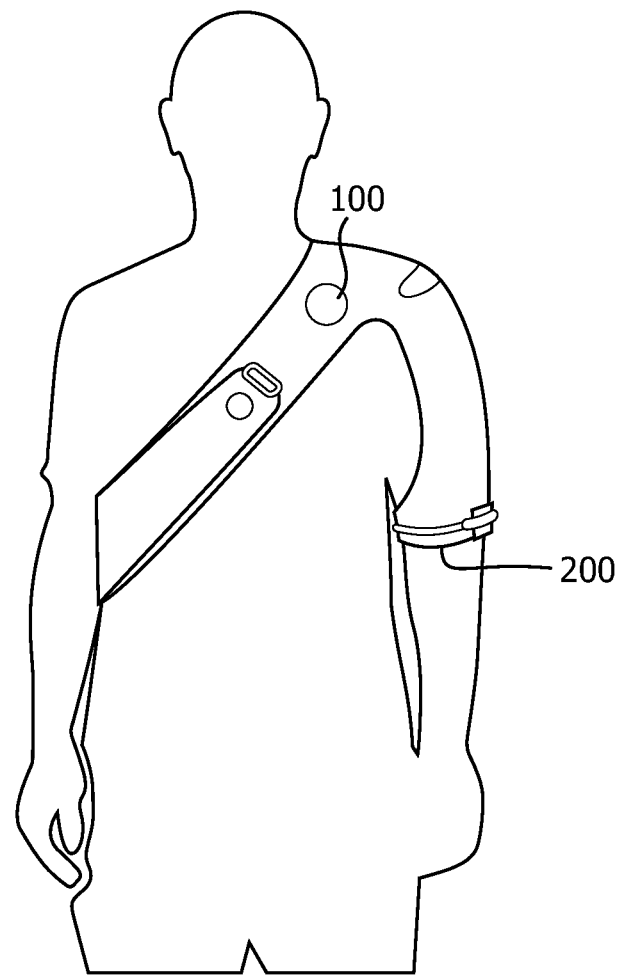
FIG. 1 shows the conventional training garment for persons with upper limb dysfunction.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

In practice, three markers (i.e., shoulder marker, elbow marker and hand marker) are necessary to be used in conjunction with the movement tracking system for persons suffering from upper limb dysfunction. However, since the present invention does not relate to the improvement of the hand marker and the improvement of the garment carrying the hand marker, the hand marker-related garment will be omitted and the training garment for the shoulder marker and the elbow marker will be described in detail in the following.

Figure 2:
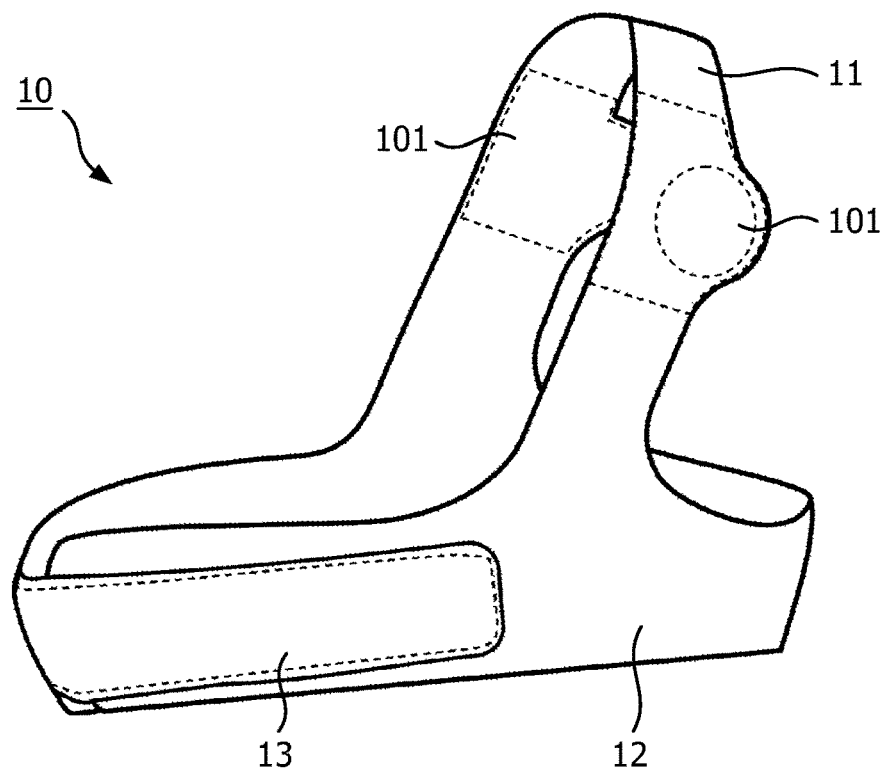
FIG. 2 shows a shoulder garment 10 in a training garment in accordance with an embodiment of the present invention.

FIG. 2 shows a shoulder garment 10 in a training garment in accordance with an embodiment of the present invention.

As shown in FIG. 2, the shoulder garment 10 basically comprises two portions, i.e., a shoulder portion 11 and a main body portion 12. In order to be distinguished from the main body portion of the elbow garment (which will be described in the following), the main body portion 12 of the shoulder garment 10 is referred to as the first main body portion 12 hereinafter. Accordingly, the main body portion of the elbow garment will be referred to as the second main body portion.

Figure 3:
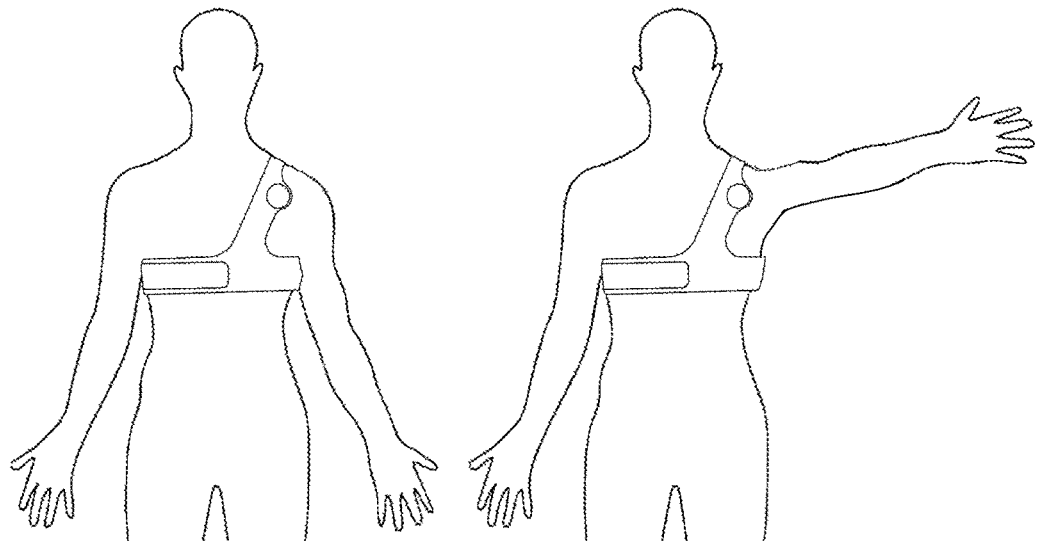
FIG. 3 shows the posture of a person wearing the shoulder garment 10 in a still state and the posture of the person when he raises his arm.

The shoulder portion 11 of the shoulder garment 10 is adapted to be worn across a shoulder of the person, as shown in the left figure of FIG. 3, which shows the posture of a person wearing the shoulder garment 10 in a still state. Further, the first main body portion 12 is adapted to be worn around the trunk of the person, as shown in the left figure of FIG. 3. Although in FIG. 3, the first main body portion 12 is shown as being worn around the chest of the person, another part of the trunk could also be possible. For example, the first main body portion 12 may be worn around the waist of the person.

In the case of the shoulder garment 10 of the present invention, both ends of the shoulder portion 11 are attached to the first main body portion 12. Although in the present embodiment shown in FIG. 2, the shoulder portion 11 and the first main body portion 12 are formed as one piece to implement the attachment between the shoulder portion 11 and the first main body portion 12, it will be readily understood by the person skilled in the art that the attachment is not only limited to this design. For example, the shoulder portion 11 may be attached to the first main body portion 12 by connection mechanisms, such as fasteners, or stitches, as long as these two portions are fixed together.

Furthermore, as shown in FIG. 2, the shoulder portion 11 has an area 101 for receiving a shoulder marker, which is shown as the dot in FIG. 3. In the embodiment shown in FIG. 2, the area 101 is provided with a VELCRO® hook and loop fastener to attach the shoulder marker. However, it will be readily understood by the person skilled in the art that the attachment is not only limited to this design, but may be implemented by other connection mechanisms known in the art.

In addition, since the stature of patients may vary, the shoulder portion 11 in the shoulder garment 10 according to the present invention is designed to be adjustable to make sure that the shoulder marker can be positioned near the shoulder joint of the specific patient.

In the embodiment shown in FIG. 2, the first main body portion 12 has two ends, one of which is provided with a strap 13 to be attached to the other end in order to fixate the first main body portion 12 around the trunk of the person. In an example, the strap 13 is adapted to attach the first main body portion 12 by a VELCRO® hook and loop fastener.

Please note that, as can be easily understood by the person skilled in the art, the first main body portion 12 may not be provided with said strap 13. Instead, the first main body portion 12 may be an elastic unitary portion to be put on by the person. In another example, the first body portion 12 may have two ends and both ends are connected with each by other connection mechanisms, for example, fasteners, a VELCRO® hook and loop fastener.

The materials used for the shoulder portion 11, the first main body portion 12, and the strap 13, may be the same or different. For example, soft and elastic material, such as EVA, may be preferred. However, other materials may also be feasible.

As shown in the right figure of FIG. 3 showing the posture of the person when he raises his arm, due to the special design of the shoulder portion 11 and the first main body portion 12, i.e., a shoulder harness-like design, the shoulder portion 11, where the shoulder marker is attached, is fixed to the first main body portion 12, which is fixedly worn around the trunk of the person.

Figure 4:
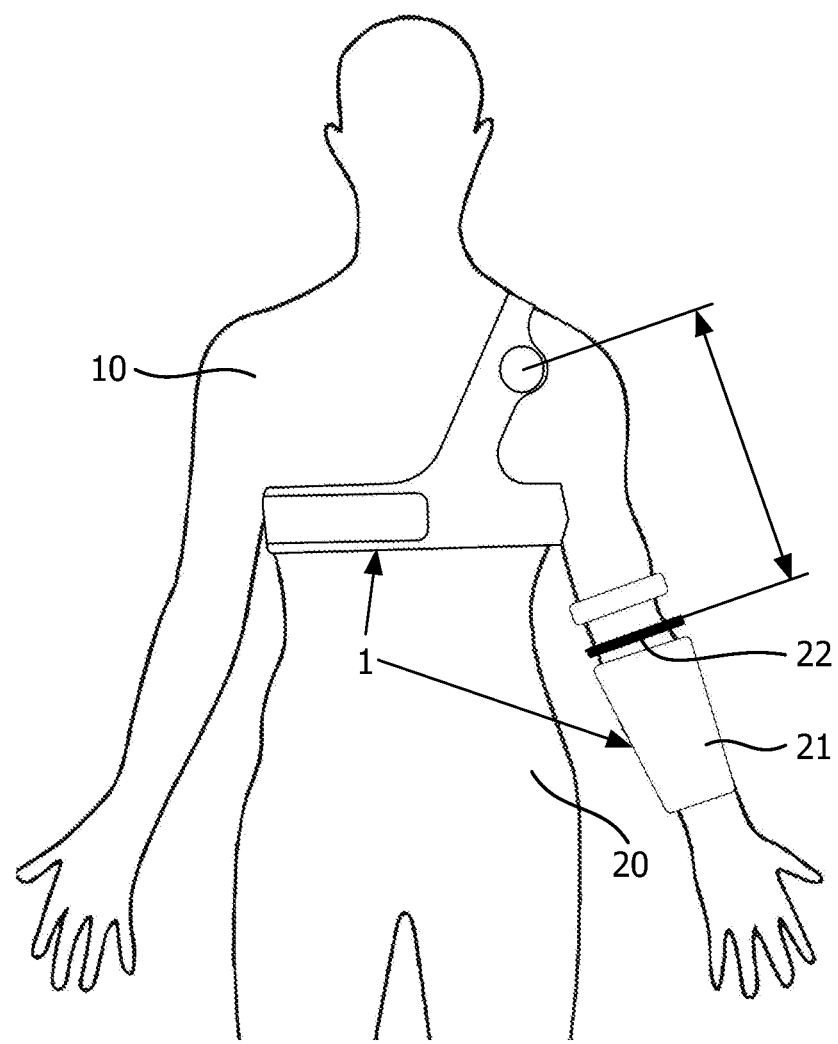
FIG. 4 shows a training garment 1 in accordance with an embodiment of the present invention, which further comprises, in addition to the shoulder garment 10, an elbow garment 20.

Therefore, the proposed shoulder garment 10 can prevent displacement of the shoulder marker while the person is performing active rehabilitation exercises, such as raising up his arm, and therefore, it can improve the recognition accuracy of the movement tracking system for the rehabilitation training FIG. 4 shows a training garment 1 in accordance with an embodiment of the present invention, which further comprises, in addition to the shoulder garment 10, an elbow garment 20. The elbow garment 20 in the present embodiment is separate from the shoulder garment 10.

The elbow garment 20 shown in FIG. 4 comprises a second main body portion 21 adapted to be worn around the upper limb of the person and an elbow marker 22, which is attached to the second main body portion 21 of the elbow garment 20 and which is adapted to be worn around the upper limb of the person near the elbow joint.

In this design, since the elbow garment 20 is separate from the shoulder garment 10, the independent elbow garment 20 ensures correct and specific calibration, because the elbow marker 22 can be accurately fixed at or near where the elbow joint is positioned, so that the movement tracking system can figure out the specific distance between the shoulder marker and the elbow marker 22 (as shown in FIG. 4). The elbow garment's individuality instead of attachment to the shoulder garment 10 removes the need for patient or caregiver to adjust its position correctly.

Therefore, in this aspect, not only the shoulder marker's displacement can be prevented, but also the elbow marker 22 can be accurately fixed. Accordingly, the recognition accuracy of the movement tracking system may be further improved.

Figure 5:
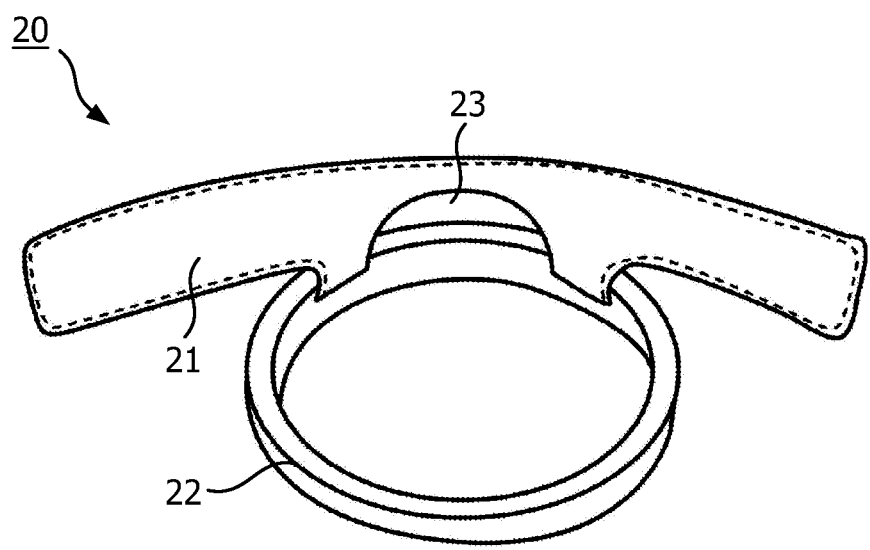
FIG. 5 is a schematic view of the elbow garment 20 in accordance with an embodiment of the present invention.

FIG. 5 schematically shows the elbow garment 20 in accordance with a preferred embodiment of the present invention.

Figure 6:
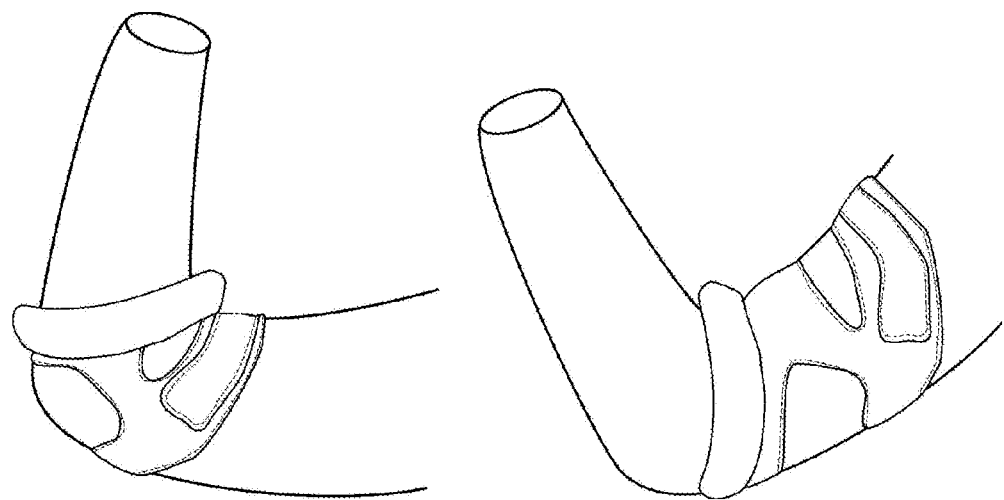
FIG. 6 shows the detailed posture when the person wears the elbow garment 20 shown in FIG. 5.

In this embodiment, unlike the conventional elbow garment, the second main body portion 21 of the elbow garment 20 further comprises a locating hole 23 for receiving the elbow joint of the person. FIG. 6 shows the detailed posture of the elbow when the person wears the elbow garment 20 shown in FIG. 5.

In this design, the locating hole 23 in the elbow garment 20 may ensure both wearing accuracy and recognition accuracy. The locating hole 23 may function as a mark designed especially to inform the person as to how he should wear the elbow garment 20, i.e. placing the elbow joint in the locating hole is the only right way to wear the elbow garment 20 (as shown in the left figure of FIG. 6). In this way, it helps the person to fixate the elbow marker 22 in the right position.

Furthermore, in this way, more of the elbow marker's external superficial area becomes exposed instead of being hidden from view(?) by the elbow joint (see the left figure in FIG. 6), as compared to the conventional elbow garment shown in the right figure of FIG. 6. Accordingly, this can further improve the recognition accuracy.

The materials of the second main body portion 21 and the elbow marker 22 may be the same or different. For example, soft and elastic material, such as EVA, may be preferred. However, other materials may also be feasible.

As mentioned above, the training garment 1 according to the present invention will be applicable for rehabilitation training of persons suffering from upper limb dysfunction, in particular, patients who survived neurological diseases like e.g. stroke or after brain surgery and orthopedic procedures.

Specifically, the procedure for wearing the training garment 1 according to the present invention may be as follows, but is not limited thereto:

1. To put on the shoulder garment 10, pass the affected arm through it and adjust the adjustable shoulder portion 11 to make sure the area 101 for the shoulder marker is just near the shoulder joint;

2. Press the strap for the shoulder marker to attach it tightly to Velcro on the area 101 of the shoulder garment 10;

3. Pass the affected arm through the elbow marker 22, making sure that the locating hole 23 is positioned at the elbow joint, and then fixate the strap for the elbow marker 22 tightly on the arm just above the elbow joint.

As can be seen from the above, the training garment 1 according to the present invention may improve the recognition accuracy of the movement tracking system for the rehabilitation training, and therefore is suitable for the early-stage patients. Moreover, the training garment 1 is also very easy to put on for a patient, especially the elbow garment 20 shown in FIGS. 5 and 6; therefore, it may be used for the later-stage patients as well.

Please note that, as mentioned above, the detailed design of the training garment 1 according to the present invention should not be limited to the design mentioned above. It will be apparent to those skilled in the art that the various aspects of the invention claimed may be practiced in other examples that depart from these specific details.

Furthermore, the mere fact that certain measures are recited in mutually different dependent claims does not indicate that a combination of these measures cannot be used to advantage.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A training garment for tracking movement in rehabilitation training for a person suffering from upper limb dysfunction, the person having a trunk, an upper limb, and an elbow joint, comprising:
   a shoulder garment, which comprises:
      a shoulder portion, adapted to be worn across a shoulder of the person; and
      a first main body portion, adapted to be worn around the trunk of the person,
      a shoulder marker to be used for movement tracking in the rehabilitation training, wherein opposing ends of the shoulder portion are attached to the first main body portion, and the shoulder portion has an area provided with a connection mechanism for receiving the shoulder marker;
   an elbow garment which is separate from the shoulder garment and which comprises:
      a second main body portion, adapted to be worn around the upper limb of the person; and
      an elbow marker to be used for movement tracking in the rehabilitation training, which is attached to the second main body portion of the elbow garment and which is adapted to be worn around the upper limb of the person near the elbow joint.

2. The training garment according to claim 1, wherein the shoulder portion is adjustable.

3. The training garment according to claim 1, wherein the first main body portion is provided with a strap to fixate the first main body portion around the trunk of the person.

4. The training garment according to claim 3, wherein the strap is adapted to attach the first main body portion by a hook and loop fastener.

5. The training garment according to claim 1, wherein the second main body portion further comprises a locating hole for receiving the elbow joint of the person.

6. The training garment according to claim 5, wherein at least one of the shoulder portion, the first main body portion, a strap connected to the first main body portion, the second main body portion, and the elbow marker is made of soft and elastic material, wherein the soft and elastic material is EVA.

7. The training garment according to claim 1, wherein the area is provided with a hook and loop fastener to attach the shoulder marker.

8. A training garment for tracking movement in rehabilitation training for a person suffering from upper limb dysfunction, the person having a trunk, and upper limb, and an elbow joint comprising:
   a shoulder garment including:
      a trunk loop adapted to be worn circumferentially around the trunk of the person,
      a shoulder strap having first and second ends attached to the trunk loop and adapted to be worn across a shoulder of the person simultaneously with the trunk loop being worn circumferentially around the trunk of the person; and
      a shoulder marker to be used for movement tracking in the rehabilitation training, wherein the shoulder strap has a connection area with a connection mechanism for receiving the shoulder marker positioned to mark the shoulder of the person when the shoulder strap is worn across the shoulder of the person simultaneously with the trunk loop being worn circumferentially around the trunk of the person.

9. The training garment of claim 8 further comprising:
   an elbow garment which is separate from the shoulder garment, the elbow garment including:
      an upper limb portion adapted to be worn around the upper limb of the person; and
      an elbow marker to be used for movement tracking in the rehabilitation training, which is attached to the upper limb portion of the elbow garment and which is adapted to be worn around the upper limb of the person near the elbow joint.

* * * * *